US012599330B2

(12) United States Patent
Kim et al.

(10) Patent No.: US 12,599,330 B2
(45) Date of Patent: Apr. 14, 2026

(54) WEARABLE MEDICAL DEVICE WITH ZONELESS ARRHYTHMIA DETECTION

(71) Applicant: WEST AFFUM HOLDINGS DAC, Dublin (IE)

(72) Inventors: Jaeho Kim, Redmond, WA (US); Pamela F. Breske, Newcastle, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 269 days.

(21) Appl. No.: 17/591,526

(22) Filed: Feb. 2, 2022

(65) Prior Publication Data

US 2022/0240832 A1 Aug. 4, 2022

Related U.S. Application Data

(60) Provisional application No. 63/144,891, filed on Feb. 2, 2021.

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/256* (2021.01); *A61B 5/282* (2021.01); *A61B 5/366* (2021.01);
(Continued)

(58) Field of Classification Search
CPC ......... A61B 5/361; A61B 5/256; A61B 5/282; A61B 5/366; A61B 5/4836; A61B 5/6802;
(Continued)

(56) References Cited

U.S. PATENT DOCUMENTS 3,724,355 A 4/1973 Busch et al.
3,724,455 A 4/1973 Unger
(Continued)

FOREIGN PATENT DOCUMENTS

DE 102005060985 A1 6/2007
EP 2305110 A1 4/2011
(Continued)

OTHER PUBLICATIONS

Shijie Zhou and Jason Gu; "Statistical Classification of Ventricular Tachycardia and Ventricular Fibrillation based on Histogram and Average Absolute Deviation;" Feb. 2013; Proceedings of the IASTED International Conference Biomedical Engineering (Year: 2013).*
(Continued)

*Primary Examiner* — Jennifer Pitrak McDonald
*Assistant Examiner* — Christopher J Mutchler
(74) *Attorney, Agent, or Firm* — Polsinelli PC

(57) ABSTRACT

Embodiments of a wearable monitoring device system can include a wearable monitoring device comprising one or more patient physiological sensors and a detector to zonelessly detect arrhythmias from physiological signals sensed by the one or more sensors, and optionally other signals. In embodiments the detector includes a processor configured with a sudden rate change onset (SRCO) algorithm, one or more arrythmia detection algorithms and, optionally, a noise detection algorithm. In embodiments, in response to detecting SRCO, the wearable monitoring device or a remote system that receives data from the wearable medical device determines whether the patient has an arrhythmia from physiological signals sensed by the one or more sensors.

20 Claims, 13 Drawing Sheets

(51) Int. Cl.

| | |
|---|---|
| *A61B 5/256* | (2021.01) |
| *A61B 5/282* | (2021.01) |
| *A61B 5/366* | (2021.01) |
| *A61N 1/04* | (2006.01) |
| *A61N 1/36* | (2006.01) |
| *A61N 1/39* | (2006.01) |

(52) U.S. Cl.
CPC .......... *A61B 5/4836* (2013.01); *A61B 5/6802* (2013.01); *A61B 5/7264* (2013.01); *A61N 1/0484* (2013.01); *A61N 1/36031* (2017.08); *A61N 1/3904* (2017.08)

(58) Field of Classification Search
CPC ............... A61B 5/7264; A61N 1/0484; A61N 1/36031; A61N 1/3904
See application file for complete search history.

(56) References Cited

U.S. PATENT DOCUMENTS

| | | | |
|---|---|---|---|
| 4,583,524 | A | 4/1986 | Hutchins |
| 4,619,265 | A | 10/1986 | Morgan et al. |
| 4,666,432 | A | 5/1987 | McNeish et al. |
| 4,698,848 | A | 10/1987 | Buckley |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Born et al. |
| 5,353,793 | A | 10/1994 | Born |
| RE34,800 | E | 11/1994 | Hutchins |
| 5,394,892 | A | 3/1995 | Kenny |
| 5,405,362 | A | 4/1995 | Kramer et al. |
| 5,429,593 | A | 7/1995 | Matory |
| 5,474,574 | A * | 12/1995 | Payne ................. A61N 1/3931 607/7 |
| 5,618,208 | A | 4/1997 | Crouse et al. |
| 5,662,690 | A | 9/1997 | Cole et al. |
| 5,708,978 | A | 1/1998 | Johnsrud |
| 5,741,306 | A * | 4/1998 | Glegyak .............. A61N 1/3904 607/12 |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,280,461 | B1 | 8/2001 | Glegyak et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,427,083 | B1 | 7/2002 | Owen et al. |
| 6,437,083 | B1 | 8/2002 | Brack et al. |
| 6,450,942 | B1 | 9/2002 | Lapanashvili et al. |
| 6,529,875 | B1 | 3/2003 | Nakajima |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,099,715 | B2 | 8/2006 | Korzinov et al. |
| 7,212,850 | B2 | 5/2007 | Prystowsky et al. |
| 7,559,902 | B2 | 7/2009 | Ting et al. |
| 7,587,237 | B2 | 9/2009 | Korzinov et al. |
| 7,753,759 | B2 | 7/2010 | Pintor et al. |
| 7,865,238 | B2 | 1/2011 | Brink |
| 7,870,761 | B2 | 1/2011 | Valentine et al. |
| 7,907,996 | B2 | 3/2011 | Prystowsky et al. |
| 7,941,207 | B2 | 5/2011 | Korzinov |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,527,028 | B2 | 9/2013 | Kurzweil et al. |
| 8,548,557 | B2 | 10/2013 | Garstka et al. |
| 8,560,044 | B2 | 10/2013 | Kurzweil et al. |
| 8,615,295 | B2 | 12/2013 | Savage et al. |
| 8,644,925 | B2 | 2/2014 | Volpe et al. |
| 8,676,313 | B2 | 3/2014 | Volpe et al. |
| 8,706,255 | B2 | 4/2014 | Phillips et al. |
| 8,742,349 | B2 | 6/2014 | Urbon et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,084,583 | B2 | 7/2015 | Mazar et al. |
| 9,089,685 | B2 | 7/2015 | Sullivan et al. |
| 9,119,547 | B2 | 9/2015 | Cazares et al. |
| 9,131,901 | B2 | 9/2015 | Volpe et al. |
| 9,132,267 | B2 | 9/2015 | Kaib |
| 9,265,432 | B2 | 2/2016 | Warren et al. |
| 9,345,898 | B2 | 5/2016 | Piha et al. |
| 9,408,548 | B2 | 8/2016 | Volpe et al. |
| 9,445,719 | B2 | 9/2016 | Libbus et al. |
| 9,454,219 | B2 | 9/2016 | Volpe et al. |
| 9,579,020 | B2 | 2/2017 | Libbus et al. |
| 9,592,403 | B2 | 3/2017 | Sullivan |
| 9,598,799 | B2 | 3/2017 | Shoshani et al. |
| 9,675,804 | B2 | 6/2017 | Whiting et al. |
| 9,724,008 | B2 | 8/2017 | Sullivan et al. |
| 9,878,171 | B2 | 1/2018 | Kaib |
| 9,895,105 | B2 | 2/2018 | Romem |
| 9,901,741 | B2 | 2/2018 | Chapman et al. |
| RE46,926 | E | 7/2018 | Bly et al. |
| 10,016,613 | B2 | 7/2018 | Kavounas |
| 10,076,656 | B2 | 9/2018 | Dar et al. |
| 10,192,387 | B2 | 1/2019 | Brinig et al. |
| 10,307,133 | B2 | 6/2019 | Kaib |
| 10,463,867 | B2 | 11/2019 | Kaib et al. |
| 10,589,110 | B2 | 3/2020 | Oskin et al. |
| 10,599,814 | B2 | 3/2020 | Landrum et al. |
| 2002/0181680 | A1 | 12/2002 | Linder et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2006/0173499 | A1 | 8/2006 | Hampton et al. |
| 2007/0142736 | A1 * | 6/2007 | Cazares ............... A61B 5/7264 600/515 |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0274148 | A1 * | 10/2010 | Zhang ................. A61N 1/3621 600/518 |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0191476 | A1 | 7/2012 | Reid et al. |
| 2012/0265265 | A1 | 10/2012 | Razavi et al. |
| 2012/0283794 | A1 * | 11/2012 | Kaib ................... A61N 1/3904 607/5 |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0079654 | A1 * | 3/2013 | Patel ..................... A61B 5/363 702/19 |
| 2013/0085538 | A1 | 4/2013 | Volpe et al. |
| 2013/0144355 | A1 | 6/2013 | Macho et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |

(56) References Cited

U.S. PATENT DOCUMENTS

| | | | |
|---|---|---|---|
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0276160 A1* | 9/2014 | Zhang | A61N 1/3956 |
| | | | 600/518 |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0273229 A1* | 10/2015 | Zhang | A61B 5/363 |
| | | | 607/7 |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |
| 2017/0312534 A1* | 11/2017 | Cao | A61N 1/3925 |
| 2017/0319862 A1 | 11/2017 | Foshee, Jr. et al. | |
| 2017/0367591 A1 | 12/2017 | Jorgensen | |
| 2018/0007983 A1* | 1/2018 | Wang | A61B 5/30 |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0282823 A1* | 9/2019 | Freeman | A61N 1/3968 |
| 2019/0321650 A1 | 10/2019 | Raymond et al. | |

FOREIGN PATENT DOCUMENTS

| | | |
|---|---|---|
| EP | 3380189 B1 | 10/2018 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012064604 A1 | 5/2012 |
| WO | 2012/151160 A1 | 11/2012 |
| WO | WO-2014149729 A1 * | 9/2014 .......... A61B 5/4836 |
| WO | 2015/056262 A1 | 4/2015 |

OTHER PUBLICATIONS

Udo Meyerfeldt et al.; "H eart rate variability before the onset of ventricular tachycardia: differences between slow and fast arrhythmias;" International Journal of Cardiology 84 (2002) 141-151. (Year: 2002).*

Gabriel E. Arrobo et al.; "An Innovative Wireless Cardiac Rhythm Management (iCRM) System;" Conference: Wireless Telecommunication Symposium, 2014 At: Washington D.C. (Year: 2014).*

Lemmert ME, Majidi M, Krucoff MW, Bekkers SC, Crijns HJ, Wellens HJ, Kosinski AS, Gorgels AP. RR-interval irregularity precedes ventricular fibrillation in ST elevation acute myocardial infarction. Heart Rhythm. Jan. 2010;7(1):65-71. doi: 10.1016/j.hrthm.2009.09.024. Epub Sep. 19, 2009. PMID: 19939739. (Year: 2009).*

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk (11 pages).

* cited by examiner

82
PATIENT

170

180
OUTSIDE
MONITORING
DEVICE

104

85

111

105

108

100
EXTERNAL
DEFIBRILLATOR
WITH ZONELESS
ARRHYTHMIA
DETECTOR

300
EXTERNAL
DEFIBRILLATOR
WITH ZONELESS
ARRHYTHMIA
DETECTOR

EXAMPLE SCHEMATIC OF MULTIPLE VECTOR ECG VECTORS FOR USE
BY A MONITORING DEVICE WITH ZONELESS ARRHYTHMIA DETECTION

600

900

1

WEARABLE MEDICAL DEVICE WITH ZONELESS ARRHYTHMIA DETECTION

CROSS REFERENCE TO RELATED PATENT APPLICATIONS

This patent application claims benefit of U.S. Provisional Patent Application No. 63/144,891 filed Feb. 2, 2021, and is incorporated herein by reference in its entirety for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and thus save the patient's life.

All subject matter discussed in this Background section of this document is not necessarily prior art and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present disclosure describes instances and examples of wearable monitoring systems (e.g., WCD systems), devices, systems, storage media that may store programs, and methods. This summary is provided to introduce a selection of concepts in a simplified form that are further described below. This summary is not intended to identify key features of the claimed subject matter, nor is it intended to be used as an aid in determining the scope of the claimed subject matter.

In embodiments, a wearable monitoring device can include one or more ECG electrodes and a processor. In some embodiments, the wearable monitoring device can be configured with one or more algorithms for detecting arrhythmias from ECG signals sensed from a patient wearing the device using the one or more ECG electrodes. In some embodiments, the one or more ECG electrodes are dry ECG electrodes.

In other embodiments, the wearable monitoring device can, in addition to one or more ECG electrodes, include one or more of additional sensors that include, but are not limited to, oximeters, respiration rate sensors, blood pressure sensors, accelerometers or gyroscopes, and the one or more algorithms can use other signals from such sensors in addition to or instead of ECG to detect arrhythmias.

In some embodiments, a remote system that can receive data from the wearable medical device can be configured with one or more algorithms for detecting arrhythmias.

In some embodiments, the one or more arrhythmias algorithms can include a zoneless arrhythmia detection algorithm, and other embodiments also include a noise detection algorithm. In embodiments, the zoneless arrhythmia detection algorithm uses ECG signals sensed by the one or more ECG electrodes, while other embodiments may also use data from one or more other sensors that include, but are not limited to, vital sign parameters, perfusion, SpO2, respiration rate, blood pressure, posture changes, etc.

In some embodiments, the zoneless arrhythmia detection algorithm is configured to detect a sudden rate change in the heart rate determined from one or more of the ECG electrodes and/or other sensors. For example, in some embodiments using ECG signals, a sudden rate change can be detected when the absolute value of the change in a parameter (e.g., heart rate, R-R interval, average HR, average R-R interval) over a predetermined timing value (e.g., a time, or number of samples, or number of heart) beats exceeds a predetermined threshold for that parameter. In other embodiments, other parameters and/or timing values can be used in detecting a sudden rate change.

In some embodiments, the zoneless arrhythmia detection algorithm can classify a patient's heart rhythm into one of several types of arrhythmias such as, for example, ventricular fibrillation (VF), ventricular tachycardia (VT), supraventricular tachycardia (SVT), monomorphic ventricular tachycardia (MVT).

In some embodiments the wearable monitoring device may classify and/or characterize arrhythmias using a zoneless arrhythmia detector, while in other embodiments a remote system that receives data from the wearable medical device may classify and/or characterize arrhythmias using a zoneless arrhythmia detector.

The foregoing summary is illustrative only and not intended in any way to be limiting.

DETAILED DESCRIPTION

A wearable monitoring device system according to embodiments may protect an ambulatory patient by monitoring a patient's ECG and, in some embodiments, electrically restarting the patient's heart. Such a system may have a number of components. These components can be provided separately as modules that can be interconnected, or can be combined with other components, and so on.

Figure 1:
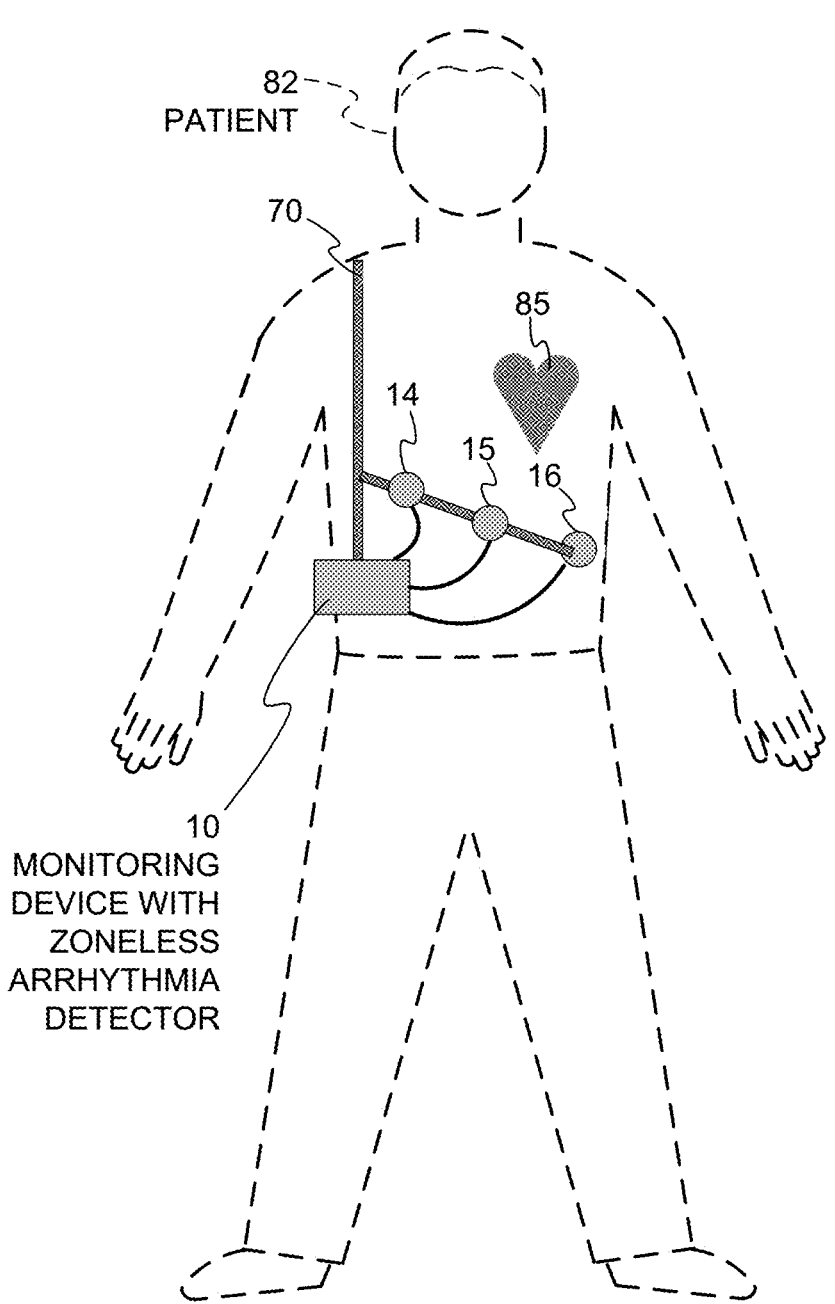
FIG. 1 is a diagram of components of a sample wearable monitoring device system with a zoneless arrhythmia detector, according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the wearable monitoring device (WMD) system, patient 82 can walk around and is not necessarily bedridden. While patient 82 may be considered to be also a "user" of the WMD system, this is not a requirement. For instance, a user of the WMD may also be a clinician such as a doctor, nurse, emergency medical technician (EMT) or other similarly tasked individual or group of individuals. In some cases, a user may even be a bystander. The particular context of these and other related terms within this description should be interpreted accordingly.

In particular, FIG. 1 also depicts components of a WMD system made according to embodiments. One such component is a support structure 70 that is wearable by ambulatory patient 82. Accordingly, support structure 70 is configured to be worn by ambulatory patient 82 for at least several hours per day, and for at least several days, even a few months. It will be understood that support structure 70 is shown only generically in FIG. 1, and in fact partly conceptually. FIG. 1 is provided merely to illustrate concepts about support structure 70, and is not to be construed as limiting how support structure 70 is implemented, or how it is worn.

Support structure 70 can be implemented in many different ways. For example, it can be implemented in a single component or a combination of multiple components. In embodiments, support structure 70 could include a vest, a half-vest, a garment, etc. In such embodiments such items can be worn similarly to analogous articles of clothing. In embodiments, support structure 70 could include a harness, one or more belts or straps, etc. In such embodiments, such items can be worn by the patient around the torso, hips, over the shoulder, etc. In embodiments, support structure 70 can include a container or housing, which can even be waterproof. In such embodiments, the support structure can be worn by being attached to the patient's body by adhesive material, for example as shown and described in U.S. Pat. No. 8,024,037. Support structure 70 can even be implemented as described for the support structure of US Pat. App. No. US2017/0056682, which is incorporated herein by reference. In light of the present disclosure, a person skilled in the art will recognize that additional components of the WMD system can be in the housing of a support structure instead of being attached externally to the support structure, for example as described in the US52017/0056682 document. There can be other examples.

FIG. 1 shows a sample monitoring device 10 configured with a zoneless arrhythmia detector. Embodiments of a zoneless arrhythmia detector will be described below in conjunction with FIGS. 3-9. Monitoring device 10 can be connected to ECG electrodes 14, 15, and 16 coupled to support structure 70 as shown in FIG. 1, while in other embodiments more than three ECG are used to implement two or more ECG channels (sometime also referred to as vectors) as will be described in more detail below. In some embodiments, one or more ECG electrodes can be disposed in or on monitoring device 10 to be used with ECG electrodes coupled to support structure 70 to implement the multiple channels. In still other embodiments, three or more ECG electrodes are disposed in or on monitoring device 10 to implement multiple ECG channels.

In embodiments, ECG electrodes 14-16 can be configured to monitor patient 82 in a number of ways. For instance, monitoring device 10 and ECG electrodes 14-16 can be coupled to support structure 70, directly or indirectly. In other words, support structure 70 can be configured to be worn by ambulatory patient 82 so as to maintain at least one of ECG electrodes 14-16 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of monitoring device 10 can be considered coupled to support structure 70 directly, or indirectly via at least one of ECG electrodes 14-16.

When ECG electrodes 14-16 make good electrical contact with the body of patient 82, monitoring device 10 can monitor multiple channels of electrical activity of the patient's heart 85. Embodiments of multichannel ECG monitoring are described below in conjunction with FIGS. 4 and 5.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

In embodiments, one or more of the components of the shown WCD system may be customized for patient 82. This customization may include a number of aspects. For instance, support structure 70 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WMD system, in order to make its diagnoses more accurate, since patients' bodies differ from one another. Of course, such parameter values can be stored in a memory of the WMD system, and so on. Moreover, a programming interface can be made according to embodiments, which receives such measured values of baseline physiological parameters. Such a programming interface may input automatically in the WMD system these, along with other data.

Figure 2:
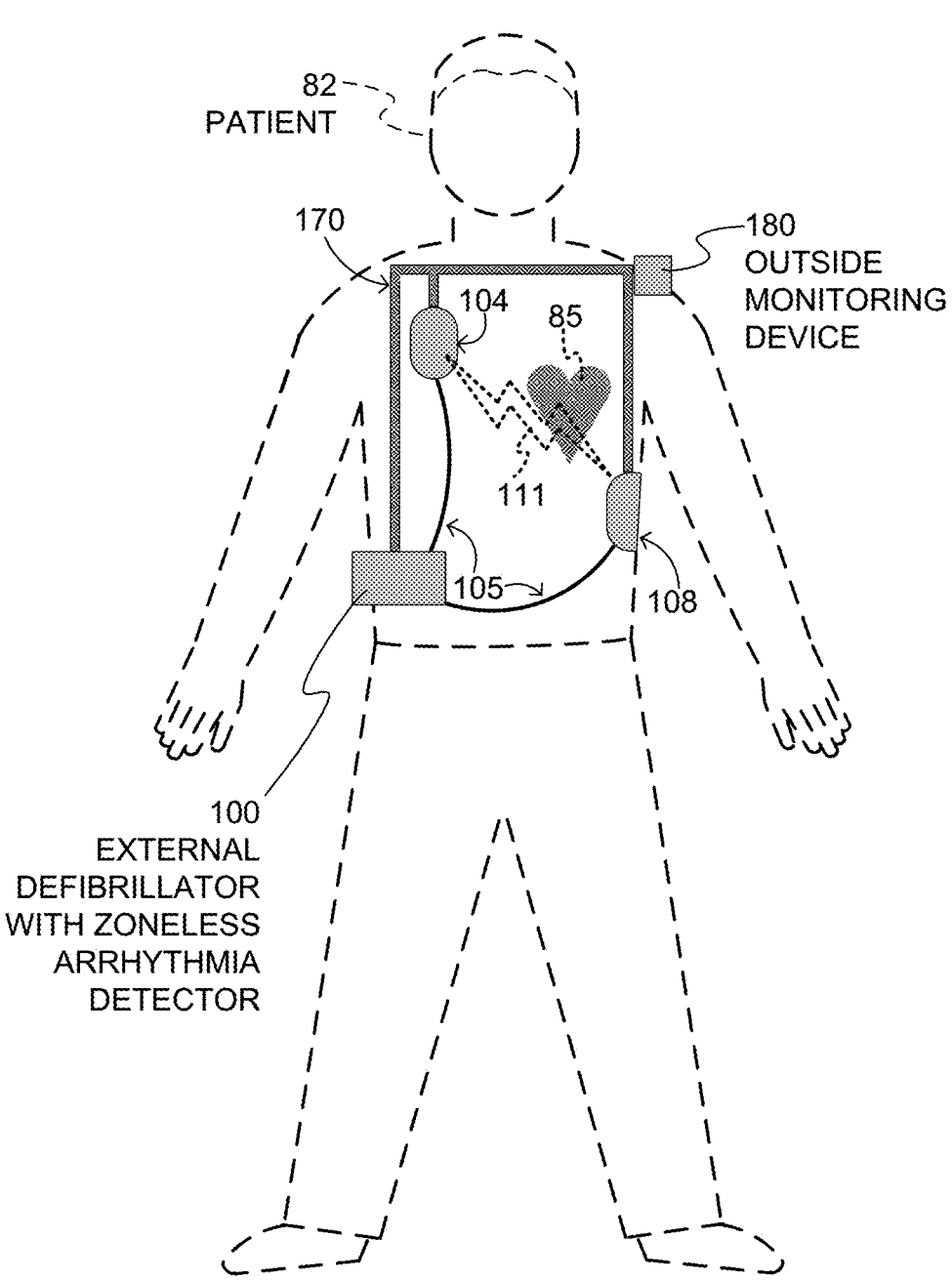
FIG. 2 is a diagram of components of a sample wearable defibrillator system with a zoneless arrhythmia detector, according to embodiments.

FIG. 2 depicts components of a wearable defibrillator system, which in embodiments includes a zoneless arrhythmia detector. Various embodiments of a zoneless arrhythmia detector are described below in conjunction with FIGS. 3-9. The wearable defibrillator system in some embodiments is a wearable cardioverter defibrillator (WCD) system is similar to the WMD system of FIG. 1, except that the wearable monitoring device is implemented using a WCD. The system includes a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 2, and in fact partly conceptually. FIG. 2 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

Embodiments of the wearable defibrillator system include an external defibrillator 100, which in embodiments includes a zoneless arrhythmia detector. As previously mentioned, various embodiments of a zoneless arrhythmia detector are described below in conjunction with FIGS. 3-9. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 2 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as patient physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 3:
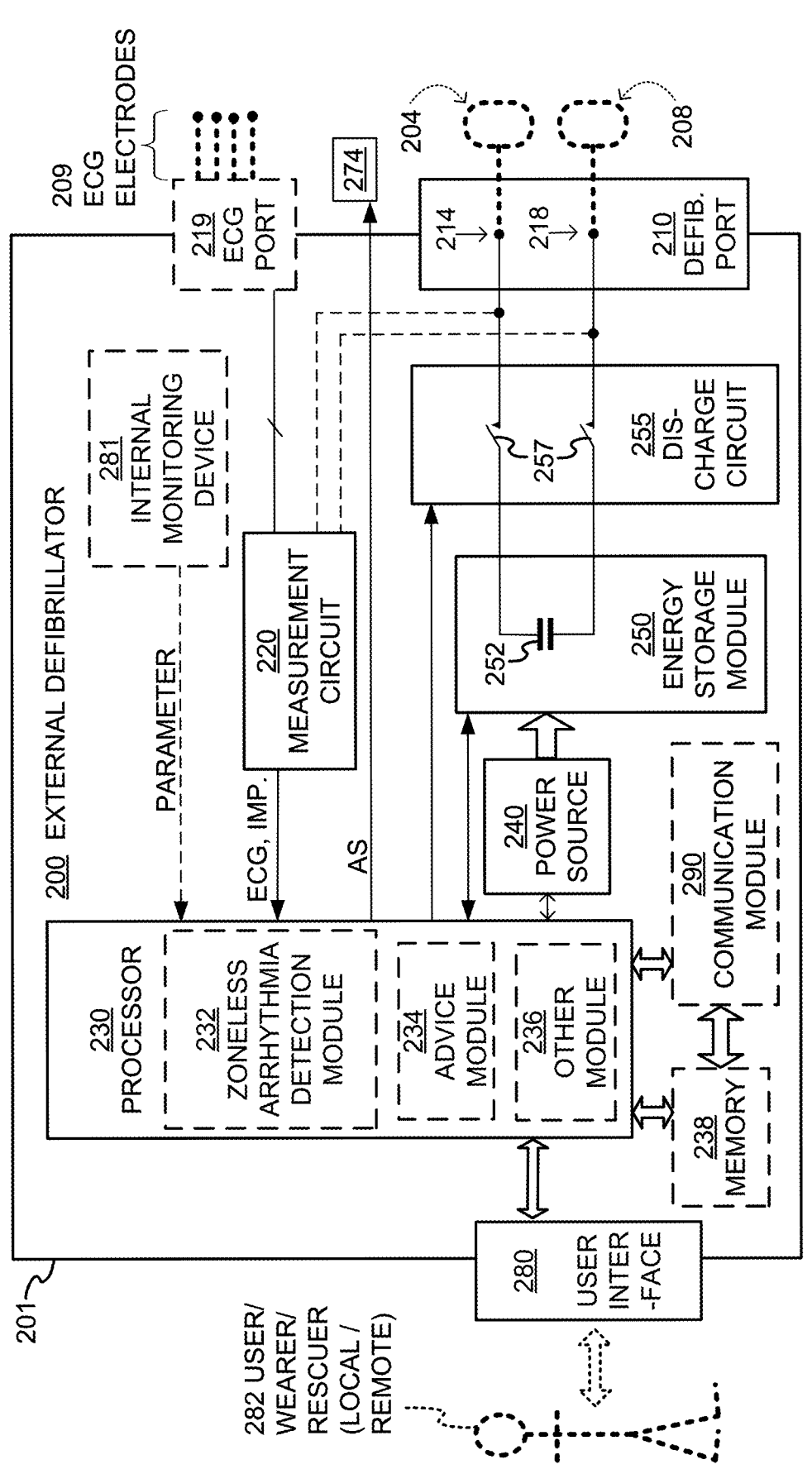
FIG. 3 is a diagram showing sample components of an external defibrillator, such as the one used in the wearable defibrillator system of FIG. 2, according to embodiments.

FIG. 3 is a diagram showing components of an external defibrillator 200, made according to embodiments. These components can be, for example, included in external defibrillator 100 of FIG. 2. The components shown in FIG. 3 can be provided in a housing 201, which may also be referred to as casing 201.

External defibrillator 200 is intended for a patient who would be wearing it, such as ambulatory patient 82 of FIG. 2. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible, or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 2. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body.

Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 2, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 3. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a zoneless arrhythmia detection module 232. Embodiments of zoneless arrhythmia detection module 232 can be configured to detect Ventricular Fibrillation (VF) without using heart rate (HR) and/or QRS width zones. In some other embodiments, HR and/or QRS width ranges can be defined to define a VF zone and optionally one or more other arrhythmia zones including for example, a Ventricular Tachycardia (VT) zone, and zoneless arrhythmia detection module 232 can be used to detect arrhythmias for rhythms outside the defined zones, including VF in a non-VF zone and/or non-VT zone in some embodiments.

The patient's sensed ECG from measurement circuit 220, which can be available as inputs, data that reflect values, or values of other signals, may be used by the zoneless arrhythmia detection module 232 to determine whether the patient is experiencing VF. Detecting VF is useful, because VF typically results in SCA. Zoneless arrhythmia detection module 232 can also detect VT, supraventricular tachycardia (SVT), monomorphic ventricular tachycardia (MVT), and so on.

Another such module in processor 230 can be an advice module 234, which generates advice for what to do. The advice can be based on outputs of zoneless arrhythmia detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018, and since published as US 2019/0030351 A1, and also in U.S. patent application Ser. No. 16/038,007, filed on Jul. 17, 2018, and since published as US 2019/0030352 A1, both incorporated herein by reference in their entireties for all purposes.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282 if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g., on a daily basis, heart rate, respiratory rate, and other vital signs data to a server accessible over the internet, for instance as described in U.S. Published Patent App. Pub. No. 20140043149A1 entitled "MOBILE COMMUNICATION DEVICE & APP FOR WEARABLE DEFIBRILLATOR SYSTEM". This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open. Defibrillator 200 can optionally include other components.

Figure 4:
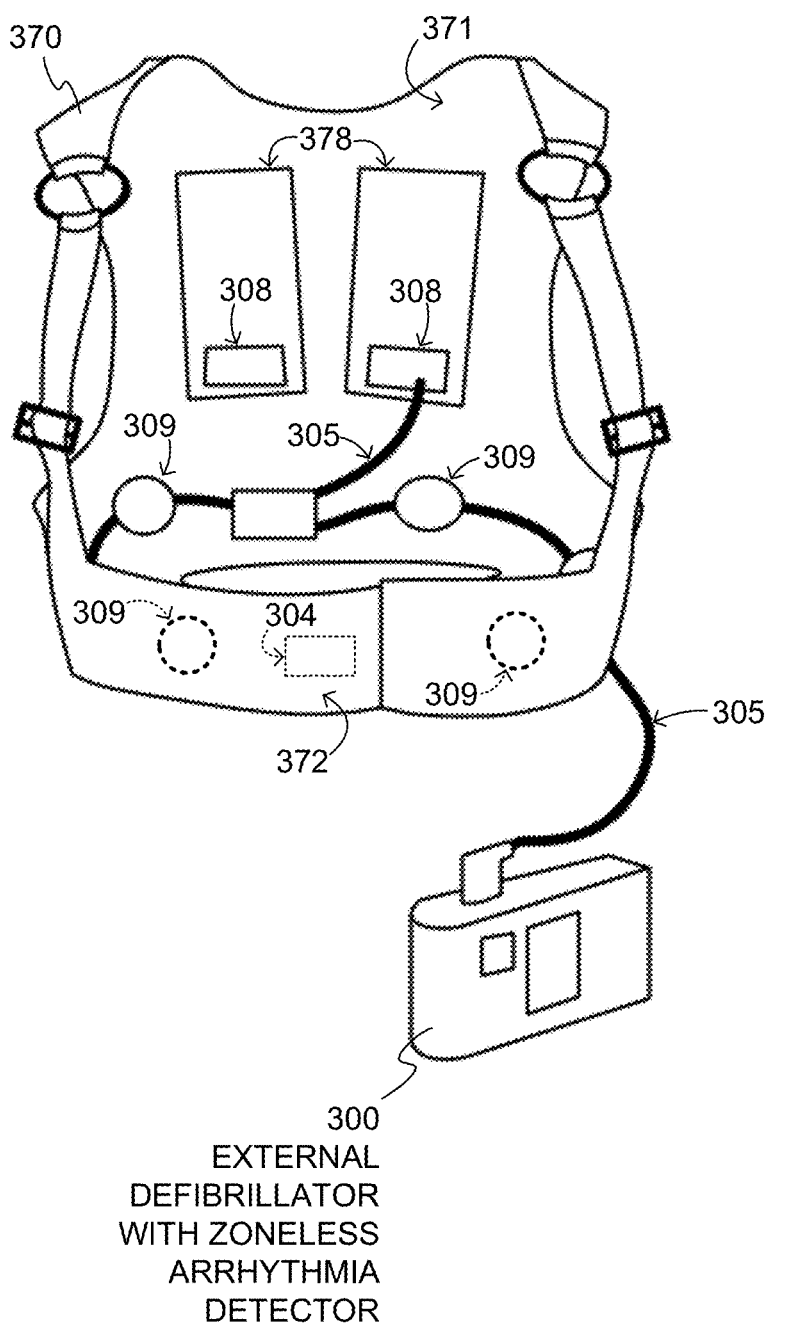
FIG. 4 is a diagram showing a sample embodiment of a multichannel WCD system, according to embodiments.

FIG. 4 is a diagram of sample embodiments of components of an WCD system with multichannel ECG monitoring. In embodiments, a support structure 370 includes a vest-like wearable garment having a back side 371, and a front side 372 that closes in front of the chest of the patient.

The WCD system of FIG. 4 also includes an external defibrillator 300, which in embodiments includes a zoneless arrhythmia detector (not shown) described further in conjunction with FIGS. 6-9. FIG. 4 does not show any support for external defibrillator 300, which in some embodiments may be carried in a purse, on a belt, by a strap over the shoulder, and so on. In other embodiments, external defibrillator 300 may be coupled to the support structure 370. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. In embodiments, back defibrillation electrodes 308 are maintained in pockets 378. In embodiments, the inside of pockets 378 can be made with a netting, so that electrodes 308 can make electrical contact the back of the patient, especially with the help of the conductive fluid that has been deployed. In some embodiments the netting can be made using conductive material. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 5:
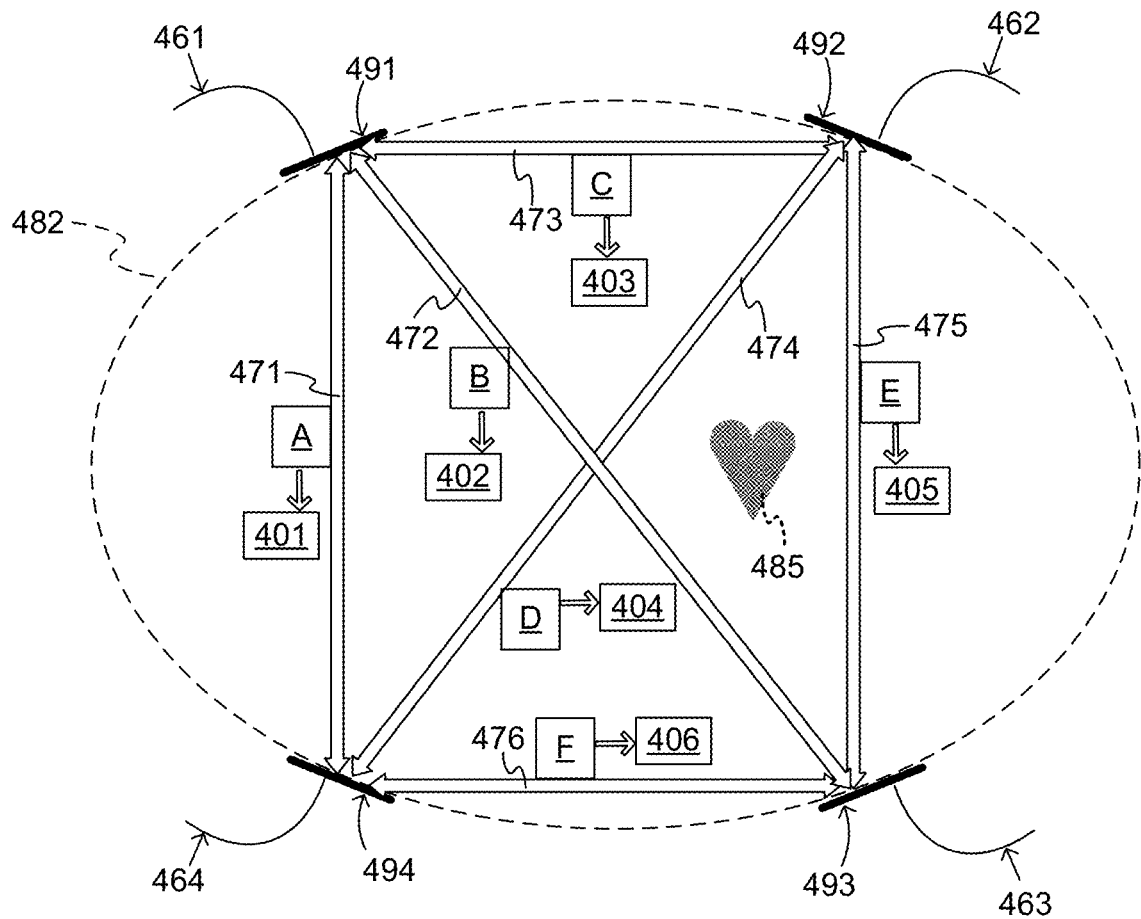
FIG. 5 is a conceptual diagram illustrating how multiple electrodes of a WCD system may be used for sensing ECG signals along different vectors, according to embodiments.

FIG. 5 is a conceptual diagram for illustrating how multiple electrodes of a WCD system may be used for sensing ECG signals along different vectors or channels, according to embodiments. As will be described below, these multiple vectors or channels can be used to zonelessly detect arrhythmias, as described below in conjunction with FIGS. 6-8. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either. Further, some embodiments average the voltages of all four electrodes electronically and then determine the voltage of each electrode relative to the average value. Conceptually this average value is the signal at some point in space in between the 4 electrodes. It continuously changes its virtual position based on the voltages of the 4 electrodes. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In embodiments, the vectors are formed in software by selecting a pair of these signals and subtracting one from the other. So for example, E1C−E2C=(E1−CM)−(E2−CM) =E1−E2+(CM−CM)=E1−E2=E12. Although six vectors are described in FIG. 4, in other embodiments a different number of vectors may be vectors may be used depending on the number of ECG electrodes used in the system and the desired number of vectors (up to the number of vectors than can be derived from the number of electrodes).

In embodiments, in order to make the shock/no-shock determination using a zoneless arrhythmia detector as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision using a zoneless arrhythmia detector, and/or to determine the patient's heart rate and/or QRS widths. For example, in some embodiments the aggregation can be implemented as disclosed in U.S. Pat. No. 9,757,581 issued Sep. 12, 2017, entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Figure 6:
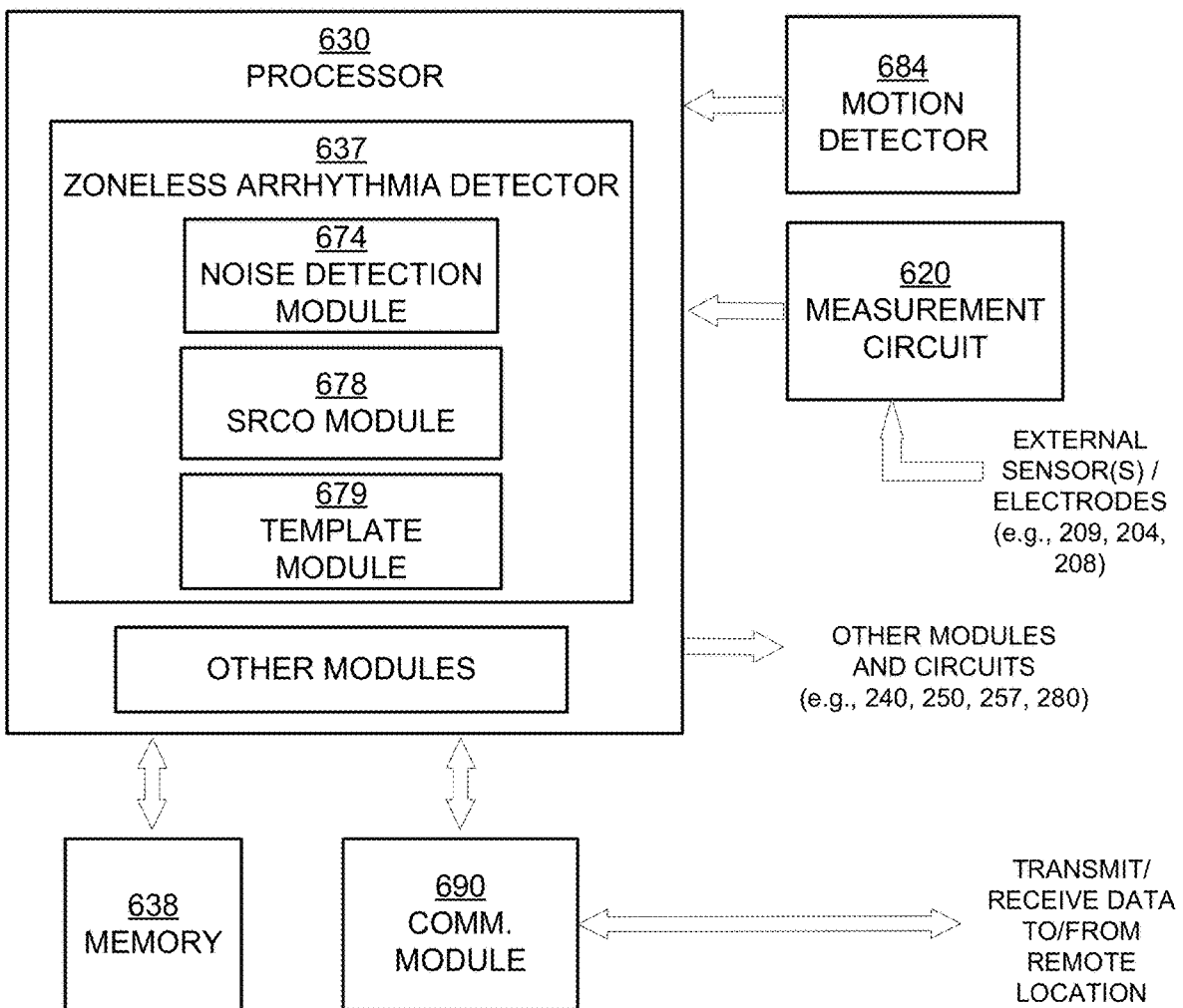
FIG. 6 is a diagram illustrating some components of a WCD system used in zoneless arrhythmia detection, according to embodiments.

FIG. 6 is a diagram illustrating some components of a WCD system with a zoneless arrhythmia detector, according to embodiments. In this example, the WCD system is similar to the WCD system of FIG. 2 and includes an external defibrillator 600 similar to external defibrillator 200 (FIG. 3).

In embodiments, external defibrillator 600 includes a measurement circuit 620, a processor 630, memory 638, motion detector 684, and a communication module 690, which are substantially similar to measurement circuit 220, processor 230, memory 238, motion detector 284, and communication module 290 described above. Other components of external defibrillator 600 (e.g., components corresponding to electrodes 204 and 208, defibrillation port 210, ECG electrodes 209, ECG port 219, power source 240, energy storage module 252, etc.) are omitted for clarity.

In embodiments, processor 630 includes zoneless arrhythmia detector module 637 and other modules as shown in FIG. 6. In embodiments, these other modules include modules (not shown) substantially similar to detection module 232, advice module 234, and other module 236 as described above for FIG. 3. Zoneless arrhythmia detector 637 has the capability of detecting and responding to changes, including sudden changes, in parameters, such as sudden heart rate change. If a sudden change is detected in one type of parameter, additional monitoring and arrhythmia determinations may be performed by embodiments of processor 630 without using zone criteria.

Zoneless arrhythmia detector 637, in some embodiments, includes a noise detection module 674, sudden rate change onset (SRCO) module 678, and a template module 679, which will be described in more detail below. In embodiments, zoneless arrhythmia detector 637 is configured to detect a sudden change in rate (also referred to herein as "sudden rate change onset" or SRCO) of a one or more sensed physiological parameter.

For example, in some embodiments, after SRCO is detected, zoneless arrhythmia detector 637 may perform additional arrhythmia determinations that include one or more of: (a) SVT detection for example by comparing the patient's ECG after the SRCO to an SVT template as disclosed in US Patent Publication US20210052181 entitled "CARDIAC MONITORING SYSTEM WITH SUPRAVENTRICULAR TACHYCARDIA (SVT) CLASSIFICATIONS"; (b) MVT detection for example by comparing the patient's ECG after the SRCO to a QRS width threshold (e.g., >0.12 seconds) and/or QRS consistency or organization such as disclosed in U.S. Pat. No. 9,592,403 entitled "WEARABLE CARDIOVERTER DEFIBRILLATOR (WCD) SYSTEM MAKING SHOCK/NO SHOCK DETERMINATIONS FROM MULTIPLE PATIENT PARAMETERS"; and/or (c) VF detection for example when the patient's ECG is neither SVT or MVT as determined in the previous two arrhythmia determinations. The aforementioned '181 publication and the '403 patent are incorporated herein by reference in their entireties for all purposes. In some embodiments, the rhythm is classified as MVT when the HR, QRS morphology and/or RR intervals determined from the ECG are stable. Further in some embodiments, a noise detection analysis as described below is performed before performing the VF detection so that noisy ECG signals will not be classified as VF.

In some embodiments, the WCD is configured to take certain actions in response to the aforementioned arrhythmia determinations. For example, in response to an SVT or MVT determination, the WCD can store a segment of ECG containing the SVT or VT and for VT enter a cardioversion process and alert an entity such as the patient, a clinician, the patient's physician etc. In addition, in response to a VF determination, the WCD can store a segment of the ECG containing the VF and enter a defibrillation shock process and alert an entity such as a clinician, the patient's physician, etc.

Returning to FIG. 6 and the description of zoneless arrhythmia detector 637, the sensed physiological parameter(s) may, for example, be derived from a patient's ECG signals sensed using an ECG sensor, such as HR or RR interval or QRS width. Other parameters can include, but are not limited to, vital sign parameters, perfusion, $SpO_2$, respiration rate, blood pressure, posture changes, etc. The parameters can be provided by one or more sensors, including but not being limited to, oximeters, respiration rate sensors, blood pressure sensors, accelerometers or gyroscopes, or other types of sensors may be used. In some embodiments, sleep apnea, for example, can be detected using the HR, activity, posture, and oximetry information. The additional physiological parameters can be used to further aid with the specificity of rhythm-to-noise detection. For example, in such embodiments, the WMD includes sensor(s) for sensing one or more of temperature, respiration, cardiac output, heart sounds, respiration sounds, oximetry, etc. For example, in some embodiments, the WMD is configured to measure the transthoracic impedance of the patient. The transthoracic impedance can be used to detect abnormal respiration, which can be used to increase the specificity of rhythm-to-noise detection.

In other embodiments, the WMD may include sensors for additional parameters such as accelerometer detected activities, for example walking, jogging, running, no motion, etc., which can also aid the WMD in decision making with regard to classifying rhythms and, in WCD embodiments, providing therapy. In embodiments in which the WCD includes an accelerometer, the accelerometer signal can be used to determine conditions as described in U.S. patent application Ser. No. 16/712,208, filed on Dec. 12, 2019, entitled "Multichannel Posture Dependent Template Based Rhythm Discrimination in a Wearable Cardioverter Defibrillator", which is incorporated herein by reference in its entirety for all purposes. For example, to increase the specificity of rhythm-to-noise detection, the accelerometer can be used to determine the following conditions: (a) the patient has a stand-up posture with walking/jogging/running activity (which may indicate the patient is conscious and should not be shocked); (b) the patient is motionless following a sudden fall (which may indicate the patient may have become unconscious and fallen and should be shocked); and/or (c) the patient is motionless but not following a sudden fall (which may indicate the patient is sleeping and should be shocked if VT or VF is detected).

As mentioned above, zoneless arrhythmia detector 637, in some embodiments, includes a noise detection module 674, sudden rate change onset (SRCO) module 678, and a template module 679. The operation of these modules is now described.

Template module 679 is configured with one or more templates for one or more arrhythmias such as, for example, SVT. Template module 679 in some embodiments creates and updates templates as described in US Patent Publication US20210052181 entitled "CARDIAC MONITORING SYSTEM WITH SUPRAVENTRICULAR TACHYCARDIA (SVT) CLASSIFICATIONS". The one or more templates may be used for SVT detection for example by comparing the patient's ECG after the SRCO to an SVT template as disclosed in the aforementioned US20210052181 publication.

Noise detection module 674 is configured with one or more noise detection algorithms to detect noisy ECG signals. In some embodiments, the noise detection analysis includes determining if the morphology and RR intervals are irregular (for example, by comparing successive QRS complexes and RR intervals against predetermined stability criteria). If the morphology and/or RR intervals are irregular, it is indicative of either VF or Noise. In some embodiments, noise is distinguished from VF by analyzing the amplitude or width of peaks in the ECG, with peaks having large amplitude and narrow width being deemed to be noise. In a more particular example, noise is deemed detected when the widths of the peaks meet one or more predetermined narrowness criteria and/or the amplitudes of the peaks meet one or more predetermined amplitude criteria. For example, noise is detected if the amplitude is larger than a predetermined factor of the normal QRS peaks, for example 5 times larger or larger than 5 mV. In some other embodiments, the noise detection algorithms can include algorithms such as described in U.S. patent Ser. No. 10/918,879B2 entitled "WEARABLE CARDIOVERTER DEFIBRILLATOR (WCD) SYSTEM REACTING TO HIGH-AMPLITUDE ECG NOISE", U.S. patent Ser. No. 10/960,220B2 entitled "WEARABLE CARDIOVERTER DEFIBRILLATOR (WCD) SYSTEM EVALUATING ITS ECG SIGNALS FOR NOISE ACCORDING TO TALL PEAK COUNTS", and U.S. Patent Application Pub. No. US20190030351A1 entitled "WEARABLE CARDIOVERTER DEFIBRILLATOR (WCD) SYSTEM REACTING TO HIGH-FREQUENCY ECG NOISE", all of which are incorporated herein in their entireties for all purposes. The output of noise detection module 674 can be used to improve specificity of arrhythmia detection for example, by eliminating noisy ECG signals from being classified as VF.

SRCO module 678 is configured to detect a sudden rate change in a parameter determined from one or more of the ECG electrodes and/or other sensors. Some embodiments of SRCO module 678 are configured with one or more algorithms to analyze ECG signals for parameters such as heart rate (HR), R-R interval, and QRS width, for example. In some embodiments, SRCO module 678 can include algorithms and processing for measuring HR, R-R interval, and/or QRS width as described in U.S. patent Ser. No. 10/105,547B2 entitled "WEARABLE CARDIOVERTER DEFIBRILLATOR (WCD) CAUSING PATIENT'S QRS WIDTH TO BE PLOTTED AGAINST THE HEART RATE" and U.S. patent Ser. No. 10/940,324B2 entitled "WEARABLE CARDIOVERTER DEFIBRILLATOR (WCD) SYSTEM COMPUTING HEART RATE FROM NOISY ECG SIGNAL", all of which are incorporated herein in their entireties for all purposes.

Figure 7:
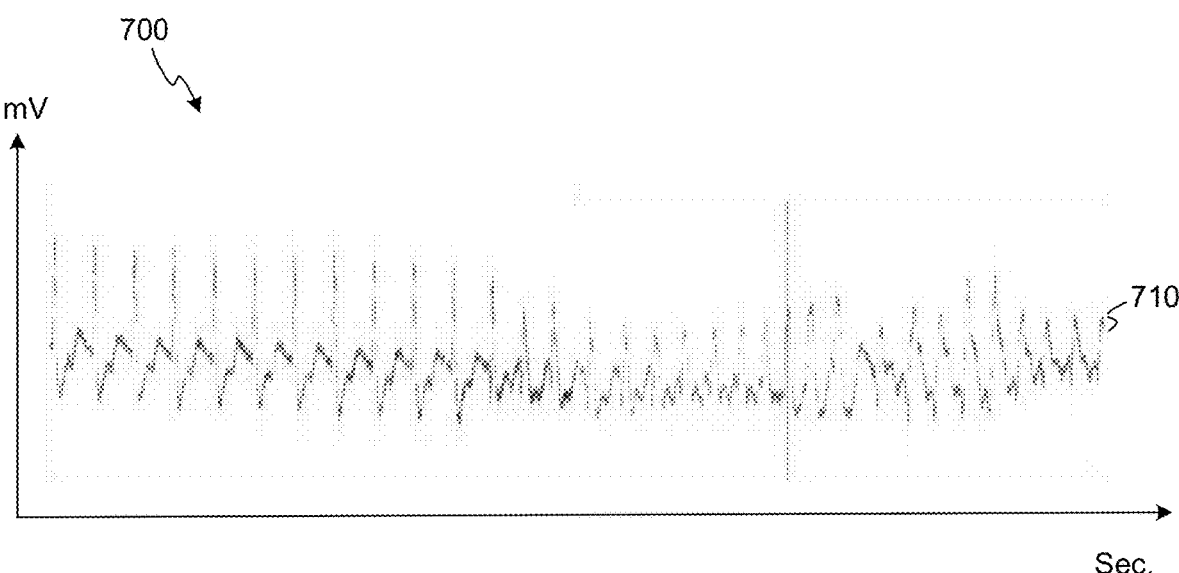
FIG. 7 is a diagram illustrating an example ECG signal detected using a wearable system, according to embodiments.
Figure 8:
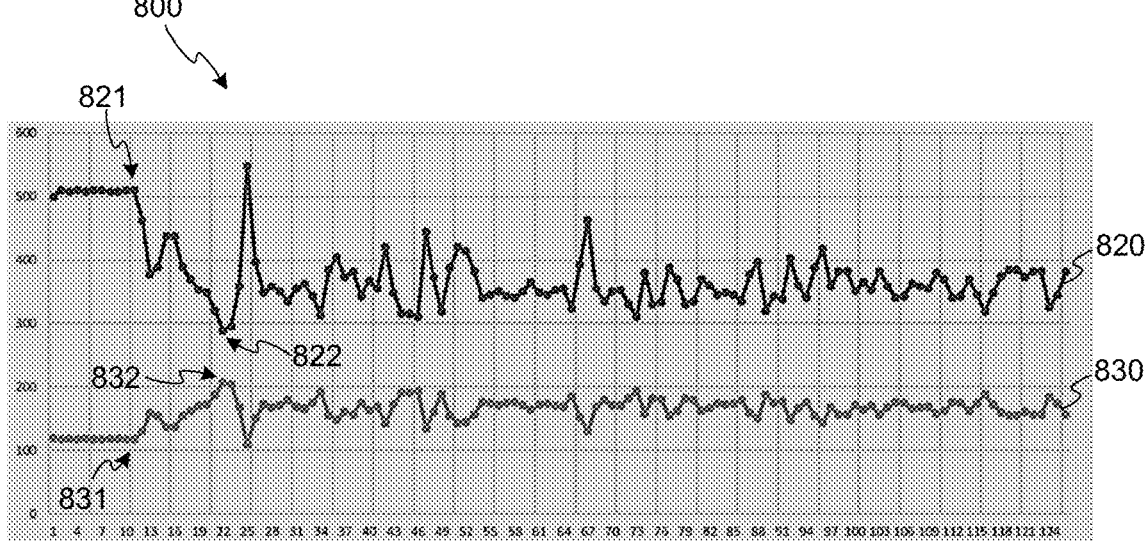
FIG. 8 is a diagram illustrating heart rate and R-R intervals of the example ECG signal of FIG. 7, according to embodiments.
Figure 9:
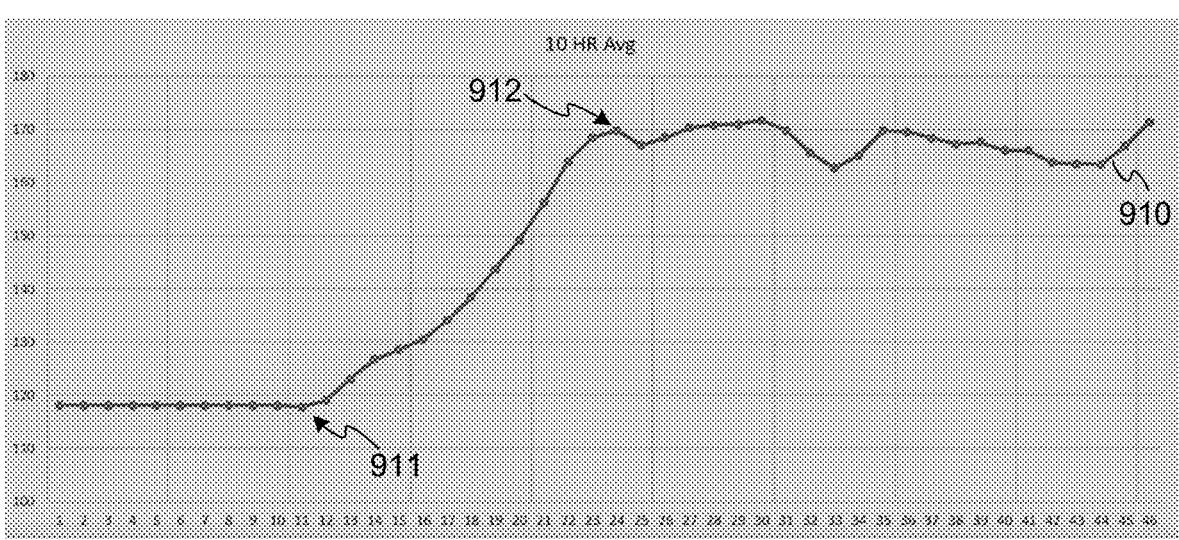
FIG. 9 is a diagram illustrating a running average heart rate of the example ECG signal of FIG. 7, according to embodiments

For example, in some embodiments in which the physiological parameter is based on ECG signals, SRCO module 678 detects a sudden rate change when the absolute value of the change in the parameter (e.g., heart rate, R-R interval, average HR, average R-R interval) over a timing value (e.g., a time, or number of samples, or number of heart beats) exceeds a predetermined threshold for that parameter. In some embodiments, the timing value has a predetermined duration or a predetermined minimum duration. FIG. 7 shows an example ECG strip 700, with an ECG signal 710 sensed from a patient experiencing an SRCO. FIG. 8 shows a chart 800 with an R-R waveform 820 and a HR waveform 830 that were determined from ECG signal 710. FIG. 9 shows a chart of a waveform 910 representing a running average of the HR measurements that were determined from ECG signal 710, in which each point on waveform 910 represents the average of the HR measurement at that time and the previous nine HR measurements. In other embodiments, the running average may be determined from a different number of previous HR measurements such as, for example, 5 to 15 previous HR measurements.

In some embodiments, when the measured physiological parameter experiences a change that exceeds a predetermined threshold, SCRO module 678 outputs a signal indicating that it has detected SCRO. In some embodiments in which the measured parameter is HR, the predetermined threshold is a change of eighty bpm over twelve HR samples. In some embodiments, the HR samples are generated 2.4 second apart. This threshold is met in HR waveform 830 in the range of measurements indicated by arrows 831 and 832. In other embodiments, the HR change ranges from 10 bpm to 50 bpm and the range of HR samples ranges from 10 samples to 20 samples. In some embodiments R-R interval is used instead of HR, with a predetermined threshold being, for example, 200 ms over twelve R-R interval samples. This threshold is met in R-R interval waveform 820 as indicated by arrows 821 and 822. In yet other embodiments, the predetermined threshold is based on a running average of the HR or R-R interval measurements. In some embodiments, the predetermined threshold is a change in the running average of fifty-five bpm over twenty HR samples. In the example of running average of ten HR measurements illustrated in FIG. 9, this threshold is met in the range of averages indicated by arrows 911 and 912.

In some embodiments, to generate the HR samples, the ECG signals received by processor 630 via measurement circuit 620 are divided into segments, each of which are about 4.8 seconds in duration. In other embodiments, the segments can range from 1 to 20 seconds. In some embodiments, the segments are overlapping segments with an overlap of 50%, but in other embodiments, the overlap ranges between 0% and 50%. A HR, R-R interval, or other parameter is determined for the segment to serve as the HR sample. In still other embodiments, instead of the number of HR samples, a different timing parameter is used such as, for example, seconds, number of QRS complexes, etc.

In some embodiments, the monitoring device 10 (FIG. 1) or the external defibrillator 100 (FIG. 2) can perform these algorithms for zoneless arrhythmia detection. In some embodiments, the aforementioned devices can communicate the sensed signals (e.g., ECG signals) to a remote device (e.g., a smart device such as a smartphone or tablet or notebook computer, or a server or cloud-based service) at which the zoneless arrhythmia detection is performed.

The devices and/or systems mentioned in this document perform functions, processes and/or methods. These functions, processes and/or methods may be implemented by one or more devices that include logic circuitry. Such a device can be alternately called a computer, a processor and so on. It may be a standalone device or computer, such as a general-purpose computer, special purpose computer, or part of a device that has one or more additional functions. The logic circuitry may include a processor and non-transitory computer-readable storage media, such as memories, of the type described above in this document. Often, for the sake of convenience, it is preferred to implement and describe a program as various interconnected distinct software modules or features. These, along with data are individually and also collectively known as software. In some instances, software is combined with hardware, in a mix called firmware.

This detailed description includes flow charts, algorithms, and symbolic representations of program operations, which according to some embodiments may be implemented within at least one computer readable medium. Embodiments of flow charts described herein may implement methods, programs, software, firmware, etc.

Figure 10:
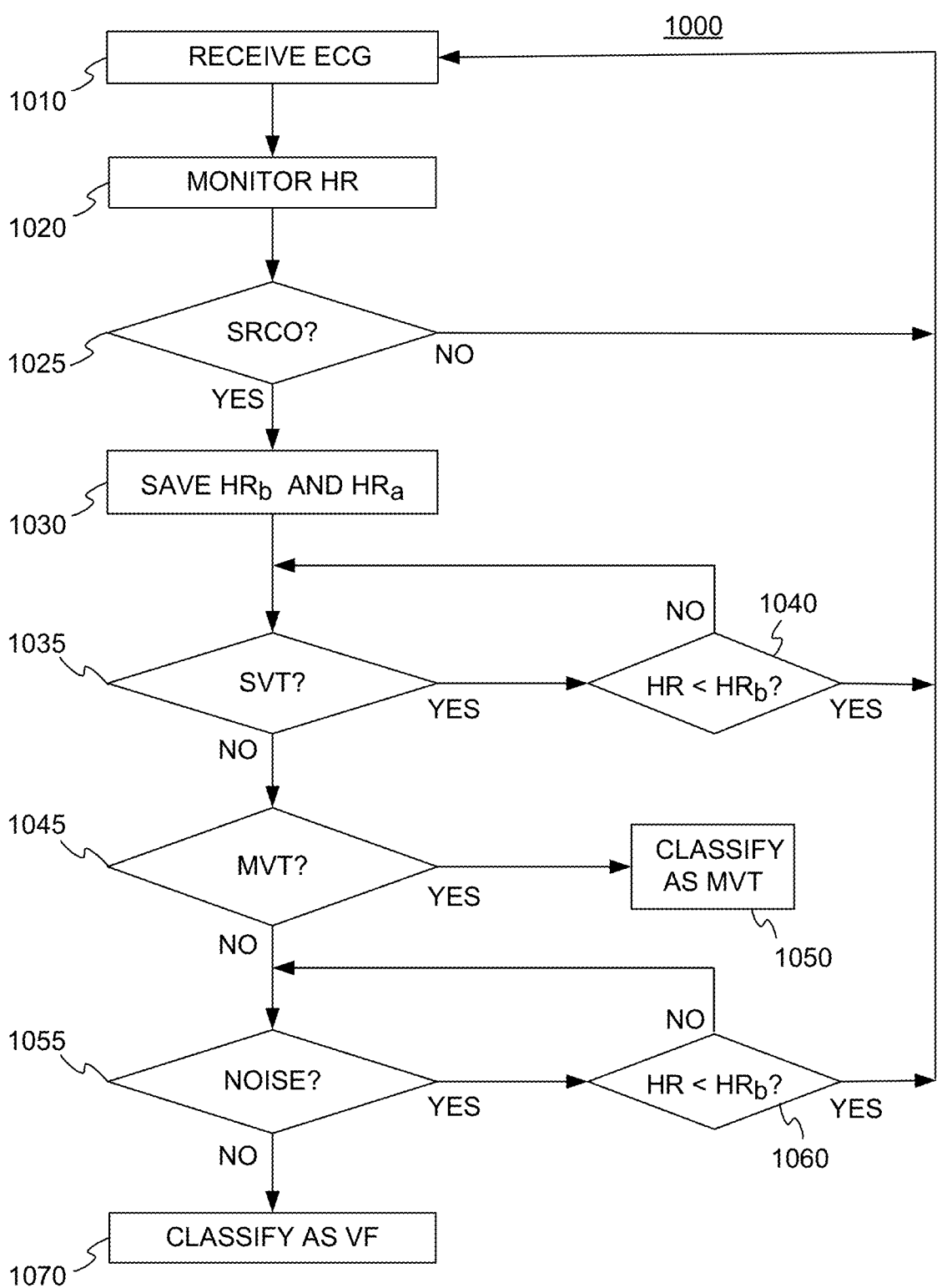
FIG. 10 is a flow diagram illustrating sample methods for use in a wearable system with zoneless arrhythmia detection, according to embodiments.

FIG. 10 is a flow diagram illustrating a method 1000 for use in a system that includes a WMD to zonelessly detect arrhythmias. In some embodiments, the WMD may be implemented using a WCD. Method 1000, in some embodiments, can start when the WMD system begins monitoring the patient's ECG. In various embodiments, the operations of method 1000 may be performed by combinations of one or more of the WMD, a remote device, a remote server, and/or a cloud-based service.

In an operation 1010 the WMD system receives ECG signals sensed from the patient using the WMD system. In some embodiments, a processor that is the same or similar to processor 630 (FIG. 6) receives the ECG signals via ECG electrodes and a measurement circuit such as ECG electrodes and measurement circuit 620 (FIG. 6). Further, in other embodiments, a remote device, a remote server, or cloud-based service can receive measurements of patient physiological parameters including ECG from a WMD, for example by wired communication, wireless communication, memory device transfer, or a combination thereof.

In an operation 1020, a patient physiological parameter is monitored. In some embodiments, the physiological parameter is the patient's HR that has been determined from the received ECG signals of operation 1010. For example, in some embodiments the HR is determined from the ECG signals as described in the aforementioned U.S. patent Ser. No. 10/105,547B2 entitled "WEARABLE CARDIO-VERTER DEFIBRILLATOR (WCD) CAUSING PATIENT'S QRS WIDTH TO BE PLOTTED AGAINST THE HEART RATE" and U.S. patent Ser. No. 10/940,324B2 entitled "WEARABLE CARDIOVERTER DEFI-BRILLATOR (WCD) SYSTEM COMPUTING HEART RATE FROM NOISY ECG SIGNAL". In other embodiments, the HR may be obtained from one or more signals other than ECG such as, for example, heart sounds, or photoplethysmography (PPG). In other embodiments, the monitored physiological parameter may be a parameter different from HR such as, for example, R-R interval, QRS width, QRS consistency, QRS organization, etc.

In an operation 1025, one or more patient physiological parameters such as, for example, HR, are analyzed to detect SRCO in the physiological parameter. In some embodiments, SRCO is detected as described above for SRCO module 678 (FIG. 6). For example, ECG signals received in operation 1010 may be analyzed for SRCO of HR or R-R interval by an SRCO detection module of the WMD that is the same or similar to SRCO module 678.

If in operation 1025 a SRCO is not detected, method 1000 returns to operation 1010 to continue receiving ECG signals. However, if in operation 1025, a SRCO is detected, method 1000 proceeds to operation 1030 in which a value of the physiological parameter before the detected SRCO ($HR_b$) and a value of the physiological parameter after the detected SRCO ($HR_a$) are saved. For example, in some embodiments, $HR_b$ and $HR_a$ are the HRs measured at the beginning and the end of the interval for determining if a rate change of the parameter exceeds the SRCO threshold as described above for SRCO module 678 (FIG. 6). Using the example shown in FIG. 8, in some embodiments, $HR_b$ is the HR at the point indicated by arrow 831 and $HR_a$ is the HR at the point indicated by arrow 832. Although these examples use HRs, in other embodiments, the parameters for $HR_b$ and $HR_a$ can be R-R intervals, QRS width, R-R variability, or other physiological parameters measured or determined before and after the SRCO is detected, respectively. Also, in some embodiments, $HR_a$ is not saved. Method 1000 then proceeds to an operation 1035.

In operation 1035 the ECG signals received in operation 1010 are analyzed to determine if the ECG is indicative of SVT. In some embodiments, SVT is detected using a template-based morphology analysis as disclosed in the previously mentioned U.S. patent application Ser. No. 16/712, 208, filed on Dec. 12, 2019, entitled "Multichannel Posture Dependent Template Based Rhythm Discrimination in a Wearable Cardioverter Defibrillator". In other embodiments, the WMD includes a processor configured with a template module that is the same as or similar to previously described template module 679 (FIG. 6) to determine whether the ECG is indicative of SVT.

If the ECG is indicative of SVT in operation 1035, method 1000 proceeds to an operation 1040. In operation 1040, the current value of the physiological parameter is compared to $HR_b$ to determine if the current value is less than $HR_b$. If in operation 1040 the current value of the physiological parameter is determined to be less than (or in some other embodiments, less than or equal to $HR_b$), method 1000 follows the "YES" path returning to monitoring the patient for SRCO as this result is indicative of SVT terminating. However, if the current value of the physiological parameter is greater than (or in some other embodiments, greater than or equal to) $HR_b$, method 1000 follows the "NO" path to return to operation 1035 and to continue analyzing the patient's rhythm for SVT. In some embodiments, rather than comparing the current value of the physiological parameter to $HR_b$, the current value is compared to the average of the saved before and after values; e.g., $(HR_a + HR_b)/2$), or other weighting of $HR_a$ and/or $HR_b$. In embodiments that do not use such average values, the value of $HR_a$ need not be save in operation 1030.

Returning to operation 1035, if the ECG is not indicative of SVT, method 1000 proceeds on the "NO" path to an operation 1045. In operation 1045, the ECG is analyzed to determine if the ECG is indicative of MVT. In some embodiments, the rhythm is classified as MVT when the HR, QRS morphology and/or RR intervals determined from the ECG are stable. In other embodiments, the MVT detection is the same as or similar to the MVT detection described above for zoneless arrhythmia detector 637 (FIG. 6).

If MVT is indicated, method 1000 proceeds to an operation 1050 in which the arrhythmia is classified as MVT. In some embodiments, operation 1050 continues to monitor the ECG and if the MVT sustains for a predetermined time, for example 60 seconds, the patient and/or other party will be alerted. In other embodiments, this predetermined time ranges from 30 seconds to 120 seconds. However, if MVT is determined to be not indicated in operation 1045, method 1000 proceeds to an operation 1055. Further, in some embodiments of operation 1050, when MVT is no longer detected, the process may also proceed to operation 1055.

In an operation 1055, one or more noise detection algorithms are performed on the ECG. In some embodiments, the one or more noise detection algorithms are the same as or similar to the those implemented in zoneless arrhythmia detector 637 (FIG. 6) and/or noise detection module 674 (FIG. 6). If in operation 1055 noise is detected, method 1000 proceeds to an operation 1060.

In operation 1060, the current value of the physiological parameter is compared to $HR_b$ to determine if the current value is less than $HR_b$. If the current value less than (or in some other embodiments, less than or equal to) $HR_b$), method 1000 follows the "YES" path cycling back to operation 1010 to receive more ECG signals. However, if the current value is greater than (or in some other embodiments, greater than or equal to) $HR_b$, method 1000 follows the "NO" path to return to operation 1055 and continue analyzing the ECG for noise. This may occur for example if the patient's HR slows down enough to take the sudden rate change back to a non-tachy level. In some embodiments, rather than comparing the current value of the physiological parameter to $HR_b$, the current value is compared to an average of the saved before and after values such as, for example, $(HR_a+HR_b)/2$, or other weighting of $HR_a$ and/or $HR_b$.

Returning to operation 1055, if noise is not detected, method 1000 proceeds to an operation 1070 in which the ECG is classified as VF. In WCD embodiments, operation 1055 will cause the WCD to perform its VF process in which the patient is shocked if patient is unconscious or otherwise cannot activate the WCD's abort mechanism.

As can be seen, the embodiments as described above can be zoneless; that is, capable of detecting whether a patient is experiencing an arrhythmia (even a shockable arrythmia like VF) without defining a VF zone based on HR and/or other parameters. Further, the operations of method 1000 may be performed by various combinations of the WMD, a remote device, a remote server, or cloud-based service.

Figure 11:
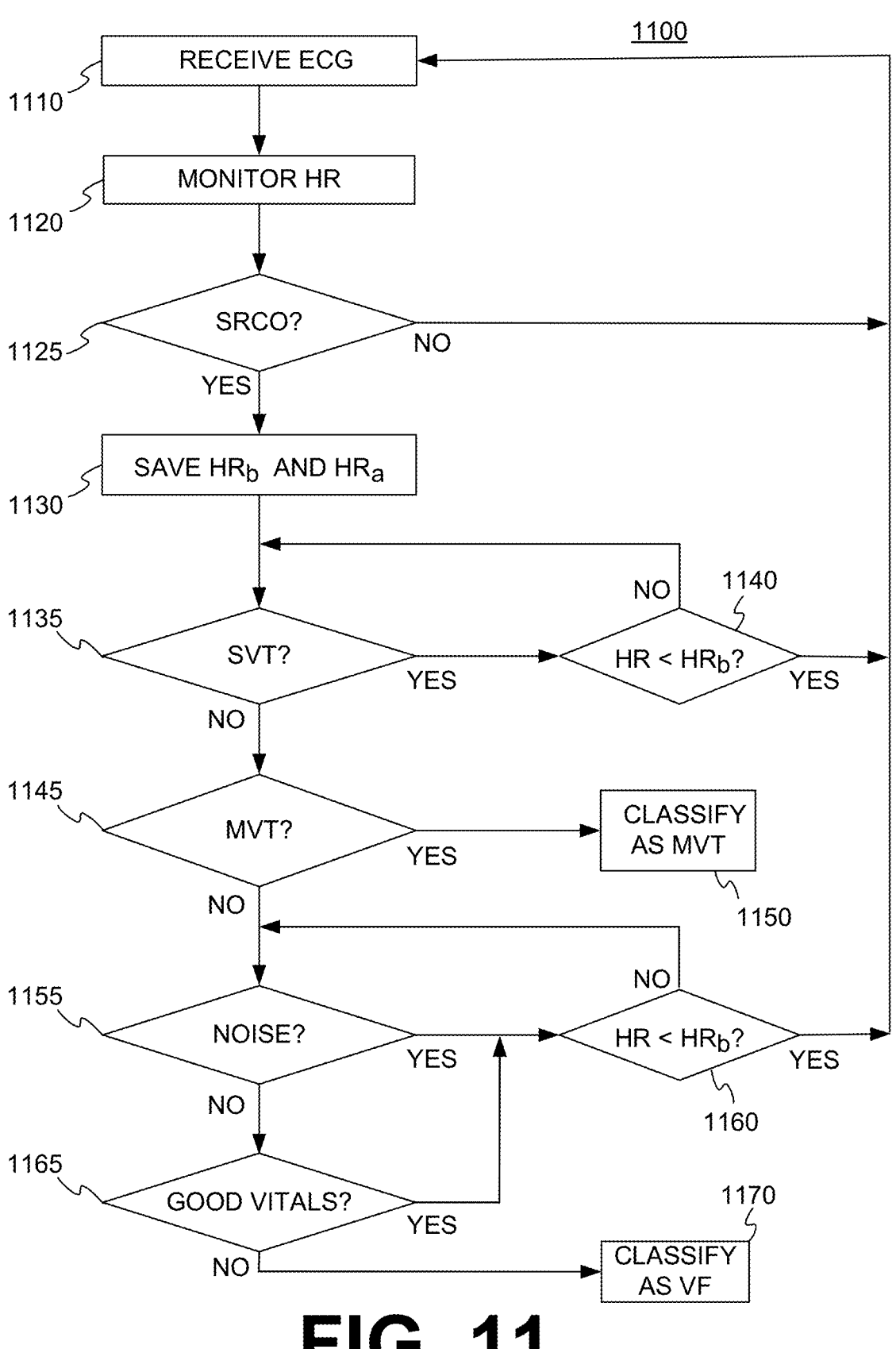
FIG. 11 is a flow diagram illustrating sample methods for use in a wearable system with zoneless arrhythmia detection and other sensors, according to other embodiments.

FIG. 11 is a flow diagram illustrating a method 1100 for use in a system that includes a WMD to zonelessly detect arrhythmias, according to some embodiments. In some embodiments, the WMD may be implemented using a WCD. In various embodiments, the operations of method 1100 may be performed by combinations of one or more of the WMD, a remote device, a remote server, and/or a cloud-based service.

Embodiments of method 1100 are similar to embodiments of method 1000 (FIG. 10) with the addition of an operation to analyze other patient physiological parameters such as, for example, the patient's vital signs. In some embodiments, the additional patient parameters are used as described above for zoneless arrhythmia detector 637 (FIG. 6). More specifically, operations 1110, 1120, 1125, 1130, 1135, 1140, 1145, 1150, 1155, 1160 and 1170, respectively, are the same or similar to operations 1010, 1020, 1025, 1030, 1035, 1040, 1045, 1050, 1055, 1060 and 1070 described above in conjunction with FIG. 10. However, compared to method 1000 (FIG. 10) in which NOISE? operation 1055 proceeds to CLASSIFY AS VF operation 1070 in the "NO" path, in method 1100 (FIG. 11) an operation 1165 is "inserted" in the "NO" path between NOISE? operation 1155 and CLASSIFY AS VF operation 1170 the "NO" path.

In operation 1165, one or more other patient physiological parameters such as, for example, the patient's vital signs are analyzed to determine if they indicate the patient is not experiencing a shockable rhythm. For example, in WCD embodiments, the vital signs may indicate the patient is perfusing and breathing (i.e., are "good"), and therefore does not need therapy. If the one or more patient physiological parameters are "good", method 1100 loops to operation 1160, which as previously mentioned is similar to operation 1060 described above in conjunction with FIG. 10. However, if the patient physiological parameters are not "good", method 1100 proceeds to operation 1170, which as previously mentioned is the same or similar to operation 1070 described above in conjunction with FIG. 10.

Figure 12:
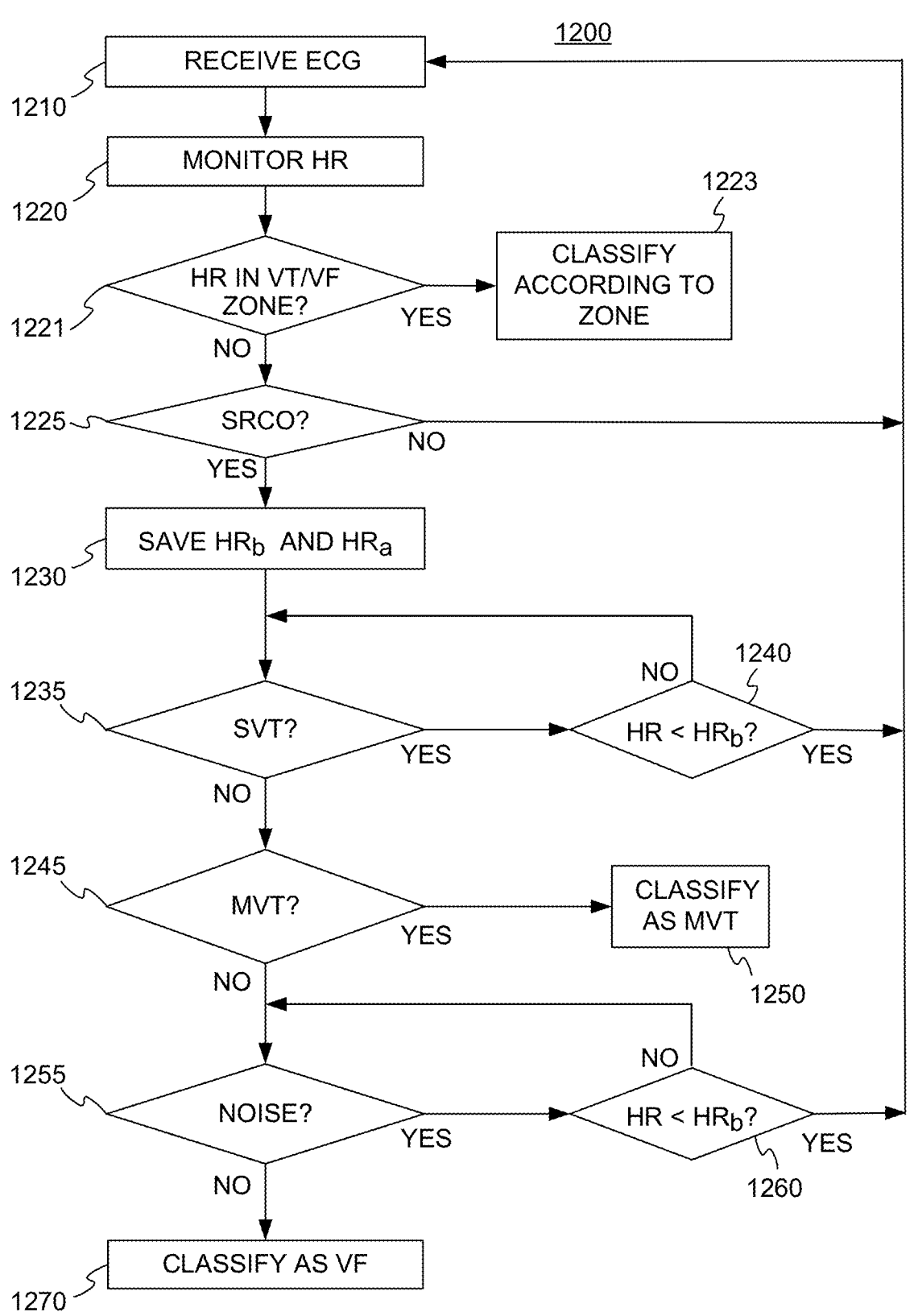
FIG. 12 is a flow diagram illustrating sample methods for use in a wearable system with zone-based and zoneless arrhythmia detection, according to embodiments.

FIG. 12 is a flow diagram illustrating a method 1200 for use in a system that includes a WMD to combine a zone-based analysis and a zoneless analysis to detect arrhythmias for ECG falling outside of the zones, according to some embodiments. In some embodiments, the WMD may be implemented using a WCD. In various embodiments, the operations of method 1200 may be performed by combinations of one or more of the WMD, a remote device, a remote server, and/or a cloud-based service.

Embodiments of method 1200 are similar to embodiments of method 1000 (FIG. 10) with the addition of operations to analyze the ECG using VT and VF zones to implement a "hybrid" system that combines zone-based analysis and zoneless analysis. More specifically, operations 1210, 1220, 1225, 1230, 1235, 1240, 1245, 1250, 1555, 1260 and 1270, respectively, are the same or similar to operations 1010, 1020, 1025, 1030, 1035, 1040, 1045, 1050, 1055, 1060 and 1070 described above in conjunction with FIG. 10. However, compared to method 1000 (FIG. 10) in which MONITOR HR operation 1020 proceeds to SRCO? operation 1025, in method 1200 (FIG. 12) an operation 1221 is "inserted" between MONITOR HR operation 1220 and SRCO? operation 1225.

In operation 1221, one or more physiological parameters are used to classify the patient's rhythm into one of multiple zones that can include a No Shock zone, a VT zone, and a VF zone in some WCD embodiments, and in some other embodiments only VF and non-VF zones are defined. For example, some currently available WCDs use HR, or HR and QRS width, to define such zones. If the one or more patient physiological parameter(s) are determined to fall into a VT zone or a VF zone, method 1200 proceeds to operation 1223 in which the WMD classifies the rhythm corresponding to the determined zone. In some embodiments, operation 1223 may include the WMD performing other processes for VT or VF such as issuing notifications to the patient or other parties, initiating one or more therapy processes, etc.

However, if the patient physiological parameter(s) do not fall into the VT zone or the VF zone, method 1200 proceeds to operation 1225, which as previously mentioned is the same or similar to operation 1025 described above in conjunction with FIG. 10. These hybrid embodiments of method 1200 enable the WMD to avoid false negatives that sometimes occur in zone-based system when an arrhythmia does not fall into one of the define arrhythmia zones, as can sometimes happen. That is, some embodiments of method 1200 can advantageously detect arrhythmias that do not fall into the defined zones and well as the arrhythmias that do fall into the defined zones.

Figure 13:
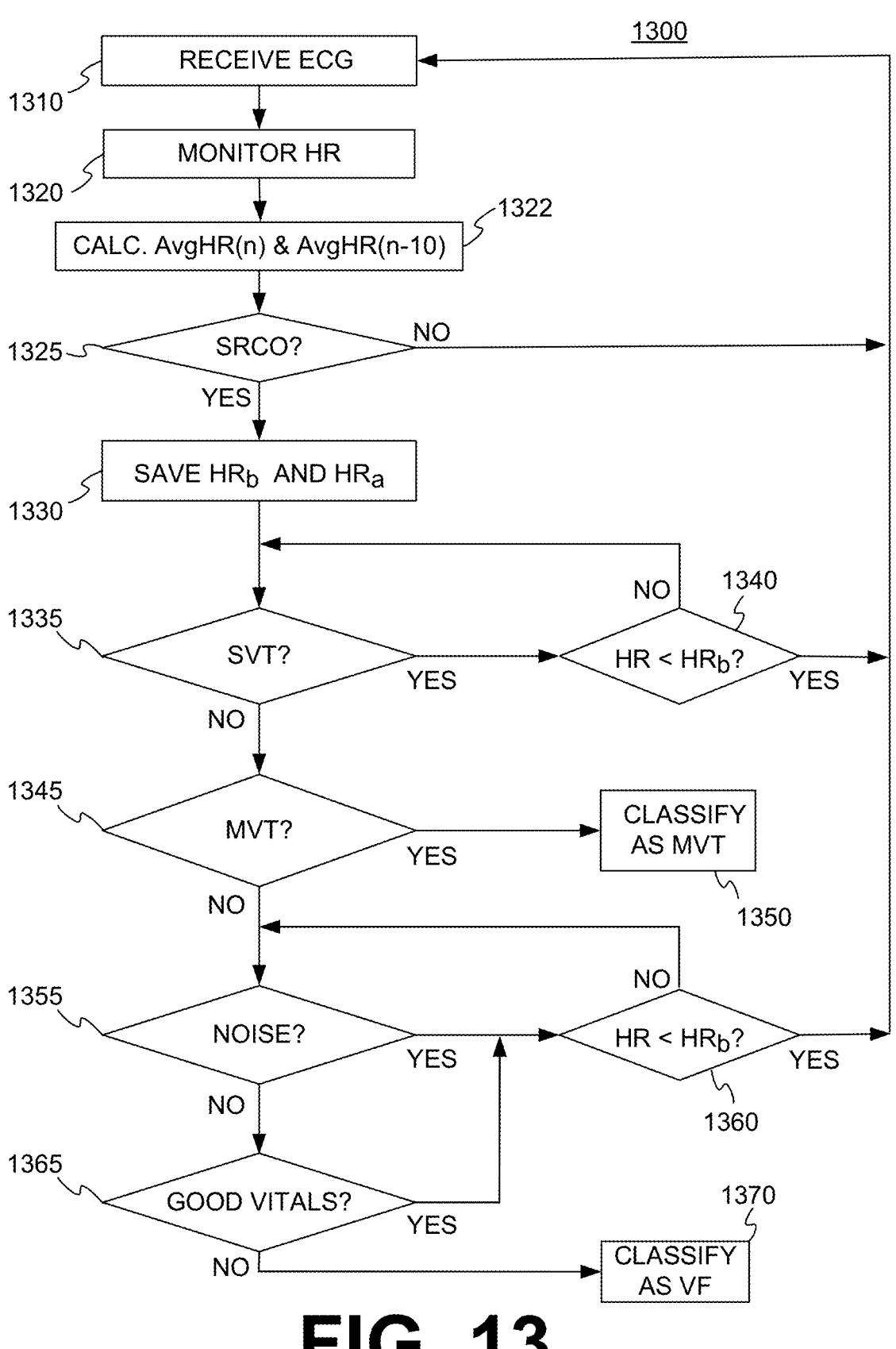
FIG. 13 is a flow diagram illustrating sample methods for use in a wearable system with zoneless arrhythmia detection using averaged heart rates, according to embodiments.

FIG. 13 is a flow diagram illustrating a method 1300 for use in a system that includes a WMD to zonelessly detect arrhythmias, according to some embodiments. In some embodiments, the WMD may be implemented using a

US 12,599,330 B2

23

24

WCD. In various embodiments, the operations of method 1300 may be performed by combinations of one or more of the WMD, a remote device, a remote server, and/or a cloud-based service.

Embodiments of method 1300 are similar to embodiments of method 1100 (FIG. 11) with the addition of an operation to determine values of HR$_a$ and HR$_b$ (e.g., see operation 1130 in FIG. 11). More specifically, operations 1310, 1320, 1335, 1340, 1345, 1350, 1355, 1360, 1365 and 1370, respectively, are the same or similar to operations 1110, 1120, 1135, 1140, 1145, 1150, 1155, 1160, 1165 and 1170, described above in conjunction with FIG. 11. However, compared to method 1100 (FIG. 11) in which MONITOR HR operation 1120 (FIG. 11) proceeds to SRCO? operation 1125 (FIG. 11), in method 1300 (FIG. 13) an operation 1322 (described below) is "inserted" between MONITOR HR operation 1320 and SRCO? operation 1325. In addition, operations 1325 and 1330 are slightly different from operations 1125 and 1130 (FIG. 11) in that the values for HR$_a$ and HR$_b$ used in operations 1325 and 1330 are determined from operation 1322 (described below) instead of using unaveraged parameters values as described in operations 1125 and 1130 (FIG. 11).

In operation 1322, running averages AvgHR(n) and AvgHR(n−10) are calculated. In some embodiments, HR(n) is a measurement or value of a patient parameter taken at time or sample "n". As previously described, the patient parameter may be heart rate, R-R interval, etc. In some embodiments, AvgHR (n) is the mean of HR(n) from n−9 to n, and AvgHR(n−10) is the mean of HR(n) from n−19 to n−10. Previously described FIG. 9 shows a graph of these running averages of heart rates for an example ECG. In other embodiments, the number of values used in calculating the average may be different. For example, in some embodiments the values for AvgHR(n) and AvgHR(n−6) are calculated, in which AvgHR(n) is the mean of HR(n) from n−5 to n, and AvgHR(n−6) is the mean of HR(n) from n−11 to n−6. Method 1300 then proceeds to operation 1325.

As previously mentioned, operation 1325 is slightly different from operation 1124 (FIG. 11) in that SRCO is detected when the absolute value of the difference of AvgHR (n) and AvgHR(n−10) exceeds a threshold value. For example, the predetermined threshold can be fifty-five bpm over twenty HR samples as previously described in conjunction with the example of FIG. 9. In some embodiments, this operation is performed by a SRCO module similar to SRCO module 678 described above in conjunction with FIG. 6. Then similar to operation 1125, if SRCO is not detected the method returns to receive more ECG signals (i.e., operation 1310 in method 1300) and if SRCO is detected the method proceeds to an operation in which values for HR$_b$ and HR$_a$ are saved (i.e., operation 1330 in method 1300). In this embodiment of operation 1330, the values for HR$_b$ and HR$_a$ are the values of AvgHR(n) and AvgHR(n−10) corresponding to when SRCO was detected in operation 1325.

In some embodiments of method 1300, operation 1365 is omitted so that vital signs are not analyzed before classifying the rhythm as VF in operation 1370, similar to method 1000 (FIG. 10).

Figure 14:
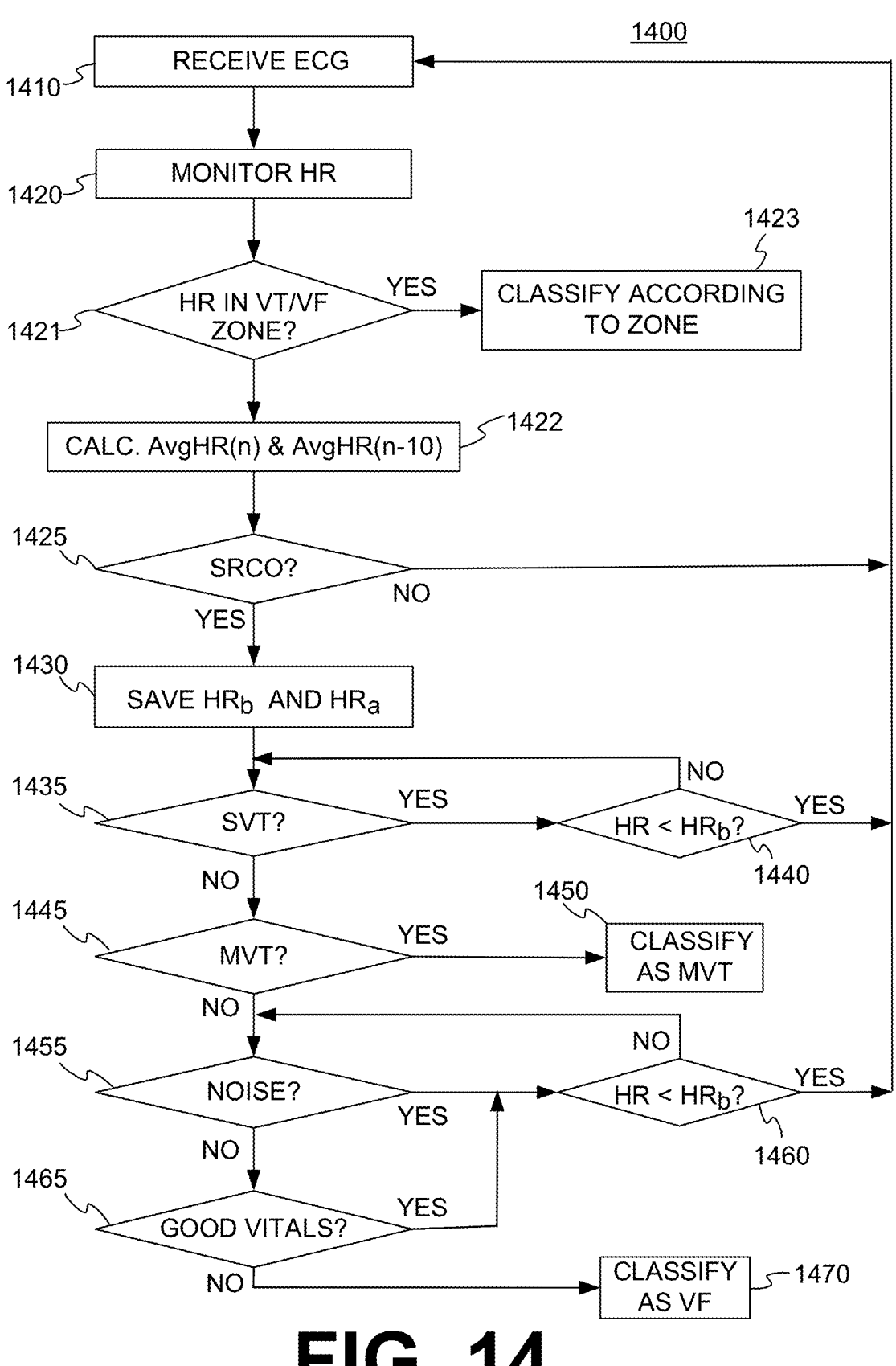
FIG. 14 is a flow diagram illustrating sample methods for use in a wearable system zone-based and zoneless arrhythmia detection using averaged heart rates, according to embodiments.

FIG. 14 is a flow diagram illustrating a method 1400 for use in a system that includes a WMD to combine a zone-based analysis and a zoneless analysis to detect arrhythmias for ECG falling outside of the zones, according to some embodiments. In some embodiments, the WMD may be implemented using a WCD. In various embodiments, the operations of method 1400 may be performed by combinations of one or more of the WMD, a remote device, a remote server, and/or a cloud-based service.

Embodiments of method 1400 are similar to embodiments of method 1200 (FIG. 12) to implement a "hybrid" system that combines zone-based analysis and zoneless analysis. In addition, method 1400 also combine the vital signs analysis operation of method 1300 (FIG. 13) and the running average operations of method 13 (FIG. 13). More specifically, operations 1410, 1420, 1421, 1423, 1435, 1440, 1445, 1450, 1455, 1460 and 1470, respectively, are the same or similar to operations 1210, 1220, 1221, 1223, 1235, 1240, 1245, 1250, 1255, 1260 and 1270 previously described above in conjunction with FIG. 12. Further, operations 1422, 1425, 1430, and 1465, respectively, are the same or similar to operations 1322, 1325, 1330, and 1365 previously described in conjunction with FIG. 13.

In the methods described above, each operation can be performed as an affirmative act or operation of doing, or causing to happen, what is written that can take place. Such doing or causing to happen can be by the whole system or device, or just one or more components of it. After careful review of this disclosure, those skilled in the art will recognize that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device, or method.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component, or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component, or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system, comprising:
  a support structure to be worn by a patient;
  an energy storage module to store an electrical charge;
  at least one therapy electrode coupled to the support structure;
  at least one sensor, coupled to the support structure, configured to generate an electrocardiogram (ECG) of the patient when the patient is wearing the support structure; and
  a processor, communicatively coupled to the at least one sensor, configured to:
    receive the ECG of the patient from the at least one sensor;
    determine, based on the received ECG, whether a heart rate and/or QRS width of the patient is within a predefined ventricular fibrillation (VF) zone, wherein the predefined VF zone corresponds to one or more ranges of the heart rate and/or the QRS width indicating VF;
    in response to a determination that the heart rate and/or the QRS width of the patient is outside the predefined VF zone, perform a sudden rate change onset (SRCO) detection of the received ECG, wherein to perform the SRCO detection, the processor is configured to:
      detect a first heart parameter value from the received ECG at a first time,
      detect a second heart parameter value from the received ECG at a second time, wherein the first heart parameter value and the second heart parameter value comprise one of a heart rate (HR), R-R interval, average HR, or an average R-R interval,
      determine a difference between the first heart parameter value and the second heart parameter value, and
      detect the SRCO of the received ECG based, at least in part, on comparison of absolute value of the difference between the first heart parameter value and the second heart parameter value with a predetermined threshold;
    responsive to the detected SRCO, perform a process to determine whether the received ECG is indicative of VF; and
    cause the energy storage module to discharge at least a portion of the stored electrical charge to the patient using the at least one therapy electrode, at least in part, in response to a determination that VF is indicated.

2. The WCD system of claim 1, wherein the processor is further configured to determine whether the received ECG is indicative of one or more of pulseless ventricular tachycardia (PVT), monomorphic ventricular tachycardia (MVT), or noise in response to the detected SRCO.

3. The WCD system of claim 1, wherein responsive to the detected SRCO, the processor is configured to:
  save the first heart parameter value, wherein the first heart parameter is detected before the SRCO;
  determine whether the received ECG of the patient is indicative of supraventricular tachycardia (SVT);
  responsive to a determination that the received ECG of the patient is indicative of SVT, determine whether a current heart parameter value determined from the received ECG of the patient is less than the saved value;

responsive to a determination that the current value is less than the saved value, detect whether the received ECG of the patient is indicative of a subsequent SRCO; and responsive to a determination that the current value is not less than the saved value, determine whether the received ECG of the patient remains indicative of SVT.

4. The WCD system of claim 3, wherein:

responsive to the received ECG of the patient being not indicative of SVT, the process further includes:

determining whether the received ECG of the patient is indicative of monomorphic ventricular tachycardia (MVT), wherein the process determines that the received ECG of the patient is determined to be indicative of VF when the received ECG of the patient is not indicative of MVT.

5. The WCD system of claim 4, wherein responsive to the received ECG being not indicative of MVT, the process further includes:

determining whether the received ECG of the patient is noisy.

6. The WCD system of claim 5, wherein the process determines that the received ECG of the patient is determined to be indicative of VF when the received ECG of the patient is determined to not be noisy.

7. The WCD system of claim 5, wherein the processor is further configured to:

determine whether a physiological parameter of the patient sensed by the at least one sensor is indicative of the patient being conscious; and classify the received ECG of the patient as VF in response to the sensed physiological parameter being not indicative of the patient being conscious.

8. The WCD system of claim 7, wherein the sensed physiological parameter comprises a vital sign.

9. The WCD system of claim 1, wherein the processor is further configured to:

not perform the SRCO detection in response to the heart rate and/or the QRS width being within the predefined VF zone.

10. The WCD system of claim 1, wherein the first heart parameter value is determined by taking an average of a first group of heart parameter values.

11. The WCD system of claim 10, wherein the second heart parameter value is determined by taking an average of a second group of heart parameter values, the second group having the same number of heart parameter values as the first group.

12. The WCD system of claim 1, wherein the WCD system further comprises an outside monitoring device configured to monitor at least one local parameter.

13. The WCD system of claim 12, wherein the at least one local parameter includes at least one of a parameter of the patient, a parameter of the WCD system, or a parameter of the environment surrounding the patient.

14. The WCD system of claim 1, wherein the first heart parameter value and the second heart parameter value correspond to the HR, wherein the predetermined threshold is a change of eighty beats per minute over twelve HR samples, wherein the first time and the second time correspond to a first and a last of the twelve HR samples respectively, and wherein the HR samples are generated at intervals of 2.4 seconds.

15. The WCD system of claim 1, wherein the first heart parameter value and the second heart parameter value correspond to the R-R interval, wherein the predetermined threshold is 200 milliseconds over twelve R-R interval samples, and wherein the first time and the second time correspond to a first and a last of the twelve R-R interval samples respectively.

16. The WCD system of claim 1, wherein the first heart parameter value and the second heart parameter value correspond to the HR, wherein the predetermined threshold is a change in a range of 10 beats per minute to 50 beats per minute over a number of HR samples, wherein the number of HR samples ranges from 10 samples to 20 samples, and wherein the first time and the second time correspond to a first and a last of the number of HR samples respectively.

17. The WCD system of claim 1, wherein the comparison of the absolute value of the difference between the first heart parameter value and the second heart parameter value with the predetermined threshold comprises the absolute value of the difference between the first heart parameter value and the second heart parameter value exceeding the predetermined threshold.

18. The WCD system of claim 1, wherein the processor is configured to detect the SRCO of the received ECG based, at least in part, on the comparison of the absolute value of the difference between the first heart parameter value and the second heart parameter value over a timing value with the predetermined threshold, and wherein the timing value comprises a time duration, a number of samples, or a number of heart beats.

19. The WCD system of claim 1, wherein the predetermined threshold is based on a running average of HR or R-R interval measurements.

20. The WCD system of claim 19, wherein the predetermined threshold is a change in the running average of fifty-five beats per minute over twenty HR samples.

* * * * *